United States Patent [19]

Cabrera et al.

[11] Patent Number: 4,702,889
[45] Date of Patent: Oct. 27, 1987

[54] LIQUID SAMPLING VALVE

[75] Inventors: Pedro P. Cabrera, Miami; Humberto A. Berra, Carol City; Edward N. Doty, Pompano Beach, all of Fla.

[73] Assignee: Coulter Electronics Inc., Hialeah, Fla.

[21] Appl. No.: 819,381

[22] Filed: Jan. 16, 1986

[51] Int. Cl.[4] .................. G01N 1/20; F16K 21/02; F16K 23/00
[52] U.S. Cl. .................. 422/103; 73/863.73; 73/864.12; 251/355
[58] Field of Search .................. 422/100, 103; 73/863.72, 863.73, 864.12, 864.83; 137/240, 246, 251.1; 251/355

[56] References Cited

U.S. PATENT DOCUMENTS

| | | | |
|---|---|---|---|
| 3,885,439 | 5/1975 | Stone | 73/863.73 |
| 3,964,513 | 6/1976 | Molner | 73/863.73 X |
| 4,152,391 | 5/1979 | Cabrera | 422/103 |
| 4,445,391 | 5/1984 | Cabrera | 422/103 X |
| 4,458,543 | 7/1984 | Mieth | 137/240 X |
| 4,507,977 | 4/1985 | Cabrera | 422/103 X |
| 4,552,167 | 11/1985 | Bräkelmann | 137/240 X |
| 4,562,748 | 1/1986 | Mrochek et al. | 73/863.73 |
| 4,587,219 | 5/1986 | Claren et al. | 422/103 X |

Primary Examiner—Michael S. Marcus
Assistant Examiner—J. Johnston
Attorney, Agent, or Firm—Silverman, Cass, Singer & Winburn, Ltd.

[57] ABSTRACT

A liquid diluting and transfer valve has disc like valve elements provided with faces frictionally engaged. The valve further includes passageways for passing both sample liquid and rinse liquid and a continuous groove formed in one of the respective faces. This continuous groove effectively isolates the passageway openings to the faces and is capable of blocking passage of leakage material along the face to the periphery of the engaged face.

11 Claims, 10 Drawing Figures

LIQUID SAMPLING VALVE

CROSS-REFERENCE TO RELATED PATENTS

This invention is an improvement to liquid transfer valve constructions such as disclosed and claimed in U.S. Pat. Nos. 4,507,977, 4,445,391 and 4,152,391 and owned by the Assignee herein. Each of these patents are incorporated by reference herein for the purpose of illustrating in detail the liquid transfer valves in which the invention herein is capable of being employed.

BACKGROUND OF THE INVENTION

This invention relates generally to liquid transfer valves particularly but not limited to those of the rotary operating type for measuring and dispensing precise microliter volumes of samples whereby a pair of measuring chambers is established in a series coupled relationship which is capable of providing simultaneously a pair of precisely measured liquid volumes and directing each to a pair of different predetermined locations, each along with a respective known volume of diluent.

More particularly, the invention provides internal passage means formed in select facing surfaces of said valve elements for isolating the passageways from the periphery of said valve elements so as to prevent liquid from reaching the circumferential exterior of the valve along said facing surfaces.

The liquid transfer metering and transfer valves such as provided in applicant's prior U.S. Pat. Nos. 4,445,391, 4,507,977 and 4,152,391 each include coaxially arranged disc members having opposite faces frictionally engaged and at least one being rotatable relative to the others.

A problem has been encountered involving the occurance of leakage apparently occasioned by liquids such as blood or diluent passing to the faces of the discs surrounding the junction between the communicating passageways and drying at the periphery of said disc surfaces. In addition to requiring disassembly of the valve assembly for cleaning with greater than normal frequency, the valve operation manifests an erratic relative rotation of the valve disc members.

Thus a need has arisen to provide means for materially reducing the frequency of maintenance by preventing such leakage, if it occurs, from traveling to the periphery of the engaged faces. Further and highly desirable is to provide means whereby the interior faces of the valve disc elements can be cleaned automatically.

The only solutions at hand in an effect to alleviate this problem were to cause the discs to be held together in face to face engagement extraordinarily tight making operation of the rotatable one of said elements extremely difficult, if not impossible. Unusual stress results on the parts which increases wear on the faces and causes premature life thereof.

SUMMARY OF THE INVENTION

An improvement in liquid transfer and/or diluting valves of the type which include at least a pair of valve elements having frictionally engaged faces and axially directed passageways each communicating in junctions at the faces; a continuous cleaning channel formed in one of the engaged faces extending substantially about the periphery of said one face but spaced inwardly thereof and bore means communicating to the end portions of the channel and to a source of rinse fluid, said channel substantially isolating the said junctions from the periphery of said faces whereby to prevent material from passing along the faces to the periphery of said faces.

DESCRIPTION OF PREFERRED EMBODIMENT

Figure 1:
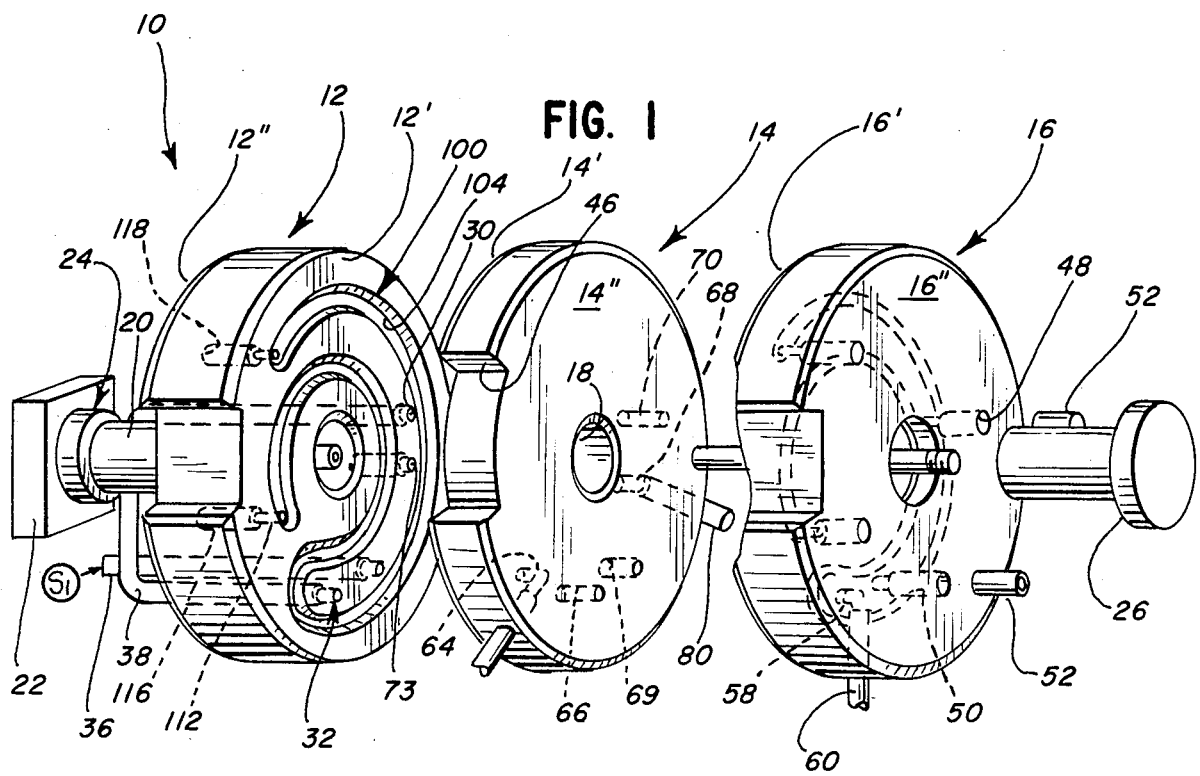
FIG. 1 is an exploded view of a liquid transfer metering and transfer valve having the improvement of the invention incorporated therein.

The invention herein will be described particularly as embodied in one of several liquid transfer valves of the type disclosed and claimed in the referenced patents. It should be understood that the invention can be employed with great advantage in those liquid transfer valve constructions which include at least a pair of valve elements having frictionally engaged faces. Passageways formed in the valve discs communicate at their junctions and liquid is passed through said passageways. The junctions of the passageways occur at the engaged faces, with rotation of the valve element causing shifting of the passageways changing the communication of one with another, as will be explained hereinafter. The invention provides a continuous cleaning channel formed in one element face, preferably one of the sandwiching disc faces, the channel functioning as a cleaning channel arranged to isolate the passageway junctions from the periphery of the engaged faces whereby to collect any leakage which may occur at the junctions preventing passage thereof to the periphery of the faces. Suitable passageway and port means are formed in the valve element communicating with the opposite ends of the continous channel whereby rinsing can be effected by introducing the rinse fluid at one end for discharge at the opposite end.

The liquid transfer valve assembly contemplated herein is capable of delivering from a single sample at least two microliter segments, preferably simultaneously, for dilution with predetermined volumes of diluent, here the segments are of different volume respectively. Passages are provided for establishing two sets of fluid paths, one set defining paths for traversal by a predetermined volume of diluent, the other set defining a series connection of a pair of precise measuring chambers of different volumes, one of which is provided by a segmenting passageway formed in the inner or movable valve element and the other being provided by an external hollow loop secured fixedly to one of the stationary members. The external loop and the feeder passageways have precise internal dimensions, preferably holding a volume in the microliter range.

Briefly, the improved valve assembly illustrated in FIGS. 1 through 4A and 4B is formed of a pair of members sealingly engaged with an inner movable member sandwiched therebetween. The valve assembly operates between a first condition during which sample is introduced from a source by way of an aspirator probe driven by an aspiration pump and a second or delivery condition. The aspirator probe can be coupled directly or through a conduit system, to a stationary portion of the valve. In the aspirating condition of the valve a continuous path is established between the aspirating probe via a segmenting passageway (constituting a first measuring chamber) and an external loop (constituting a second measuring chamber, through a connecting passageway, leading to the aspiration pump.

The valve assembly is operated to place same in the delivery condition, thereby placing the volume segmented from the continuous path by the segmenting passageway into a path established to direct diluent thereto for delivery from the valve to a selected location.

Simultaneously, the volume of sample contained in the second measuring chamber (namely the internal volume of the external loop) is coupled to a path through which diluent is introduced to sweep said volume of sample from second measuring chamber for delivery to a second preselected location.

One embodiment of the valve assembly constructed in accordance with the invention as illustrated in FIGS. 1 to 4B inclusive comprises as assembly 10 formed of a pair of coaxially arranged outer stationary disc elements 12 and 16 having a rotatably movable central valve disc element 14 sandwiched therebetween. The stationary elements 12 and 16 are arranged apart only sufficiently to accommodate the thinner central element therebetween.

First referring to FIG. 1, the outer elements 12 and 16 are provided with inner faces 12' and 16' which are engaged sealingly with faces 14' and 14" of the inner element 14. Element 12 also has an outer face 12" and element 16 has outer face 16". Faces 12', 14', 14" and 16' are machined carefully and stress relieved as by heat. All faces are provided with a hard ceramic surface to reduce friction or binding.

Each of the valve disc elements 12, 14 and 16 have central passageway 18 of the same inner diameter and all are mounted coaxially on the spindle 20 including support elements 22 and 24 and shaft 26. The mounting is described in more detail in U.S. Pat. No. 4,152,391.

In FIG. 1, the left hand element 12 carries the external hollow loop while the right hand element 16 carries either the aspirator probe directly coupled thereto or has the aspirator probe adapted to be coupled thereto by way of a conduit coupling.

A pair of axially parallel through passageways 30 and 32 are formed in stationary outer disc element 12. Another through passageway 34 is formed in disc element 12 parallel axially to the passageways 30 and 32 but angularly spaced therefrom so that a radial line taken through the axial center of passageway 34 defines a precise angle $\theta$ with a radial line taken through the axial center of passageway 32. The passageway 34 includes a short portion 34' of small diameter opening to the inner face 12' while the larger diameter portion 34' opens to the outer face 12" for receiving nipple 36 for coupling to a source of diluent.

The axial centers of passageways 30, 32 and 34 are spaced identically a radial distance "a" from the center axis of the disc 12. Passageways 30 and 32 each have a major portion 30" and 32" of larger diameter compared to the short portions 30' and 32', each of which opens to the inner face 12'. The larger diameter portions 30' and 32' open to the outer face 12" of element 12. (FIG. 2A) Passageway portions 30" and 32" have the same inner diameter.

An external hollow loop 38 is secured to the element 12 with opposite ends 38' seated tightly fully in the larger diameter passageway portions 30" and 32". The external loop 38 has a precise internal volume. The inner diameter of the hollow loop 38 preferably is uniform with the opposite ends 38' having an inner diameter equal to the diameter of the smaller passageway portions 30' and 32' of passageways 30 and 32. The ends 38' are inserted fully within passageway portions 30" and 32" to about the inner ends of passageway portions 30" and 32". Thus a precise volume of liquid can be contained within the measuring chamber 40 defined within the hollow external loop.

The stationary valve elements 12 and 16 are provided with circumferential notches 42 and 44 while center valve elements 14 is provided with a notch 46 of the same depth but encompassing a greater angular distance along the circumferential opening length than the angular extent of notches 42 and 44. Notches 42 and 44 are aligned with the opposite sides of said notches limiting the relative angular rotation of the center valve element 14 to an angular distance equal to the difference between the length of notches 42,44 and the length of notch 46. The angular rotation of the center valve element 16 required to change the valve assembly 10 from one condition to its other condition is represented by angle $\theta$.

When the valve elements 12, 14 and 16 are assembled to constitute the valve assembly 10, all of the axially directed passageways and portions thereof which communicate with other passageways carried by the valve elements are coaxial, and all are parallel to the common center axis of said elements 12, 14 and 16.

Valve elements 12, 14 and 16 are mounted coaxially on spindle 20.

A pair of like axially parallel passageways 48 and 50 are formed in the other stationary valve element 16, each passageway 48 and 50 having a larger diameter long portion 48" and 50" opening to the outer face 16" of element 16 with smaller diameter short portion 48' and 50' opening to the inner face 16' of element 16. A cylindrical nipple 52 is tightly seated within each of the large portions 48' and 50' extending outward of element 16 and opening to the exterior of the valve for coupling to the aspirator pump P and to suitable conduits leading to one of the preselected delivery locations, here to the location intended to receive the smaller segmented volume of sample.

The stationary valve element 16 also is provided with a radial bore 54 opening to the outer circumferential surface of the element 16. The inner end 54' of bore 54 communicates with a short axial bore 55 formed parallel to the axis of the valve element 16 and opening to the inner face 16' thereof. Thus bores 54 and 55 together constitute an angular passageway 58. The aspirator probe 60 is adapted to be coupled directly to the bore 54 by a conduit, or directly received within bore 54.

The rotatably movable center valve disc element 14 is provided with two pair of passageways, first pair 64 (including bore 74), 66 and second pair 68 (including bore 72), 70. Passageway 66 is formed as a through passageway of precise uniform inner diameter while passageways 64 and 68 extend in an axial direction only partially through the valve element 14 from 14' of said element. The radial bores 72 and 74 are provided in element 14 entering from the outer circumferential surface 76 thereof and communicating to the inner end 64' and 68' of the partial passageways 64 and 68. The inner diameter of bores 72 and 74 is sufficient to enable seating therein of nipples 78 and 80, one of which is capable of being coupled to a conduit 82 leading to the preselected delivery location for receiving the larger volume of sample which comprises the interior volume of the hollow loop 38 and the other (80) enabling coupling thereto of a conduit 82 leading from a source $S_2$ of diluent for directing the predetermined volume of diluent to the hollow loop 38 when the valve element 14 is rotated to place the valve 10 in its delivery condition from its load condition. Passageway 70 serves only as a communication channel to the pump, holding its content when rotated for delivery of the measured content of loop 38 and passageways 30,32.

When the valve element 14 is rotated from its load condition fo the delivery condition, the through segmenting passageway 66 which defines the smaller measuring chamber is brought into communication with the passageways 34,50 enabling a predetermined volume of diluent from source $S_1$ to be introduced via passageway 34 to drive the content of the segmenting passageway 66 to the predetermined location via passageway 50 of valve element 16. Also, when the valve is in the delivery condition, the hollow loop 38 is aligned with passageways 64,68 enabling a predetermined volume of diluent to be directed through the hollow loop 38 and deliver the contents of the loop to a predetermined location.

The disc 12 is provided with a through passageway 73 which will couple with bore 72 in number 14, leading out of valve 10. Also, the disc 14 has a through passage 69 which, in the backwash condition of the valve, will connect with passageways 34 and 50 in the front and rear disc members 12, 16 respectively. Hence in the backwash configuration, rinse fluid can be applied from the left side of FIG. 1 into the passageway 73 (as well as into the said passageway 34), which leads into the passageways 69 and bore 72, then out of the valve 10 at selected locations.

The valve 10 returns to the original aspiration condition but fulfills the backwash mode of operation. The disc 14 has been rotated after the delivery has been completed, to place passageway 73 in communication with the passageway defined by bores 68, 72 of disc 14. In this condition, the passageway defined by bores 64,74 is placed out of communication with passageway 30. The sample in passageway 66 has been delivered with passageway 66 being returned to communicate to the passageway 58 leading to the probe 60. Passageway 69 is returned to communicate with passageways 34 and 50. Passageway 70, with its isolated content, is returned to communication with passageways 48 and 30. The rinse liquid is directed from a source through the aligned passageways of the valve 10 to predetermined locations. Passageways 34, 50 provide means of rinsing passageway 69 in the backwash or rinse mode. Passageway 73 is provided to permit rinse or backwash of the passageway defined by bores 68, 72 in element 14.

Figures 2, 2A, 2B:
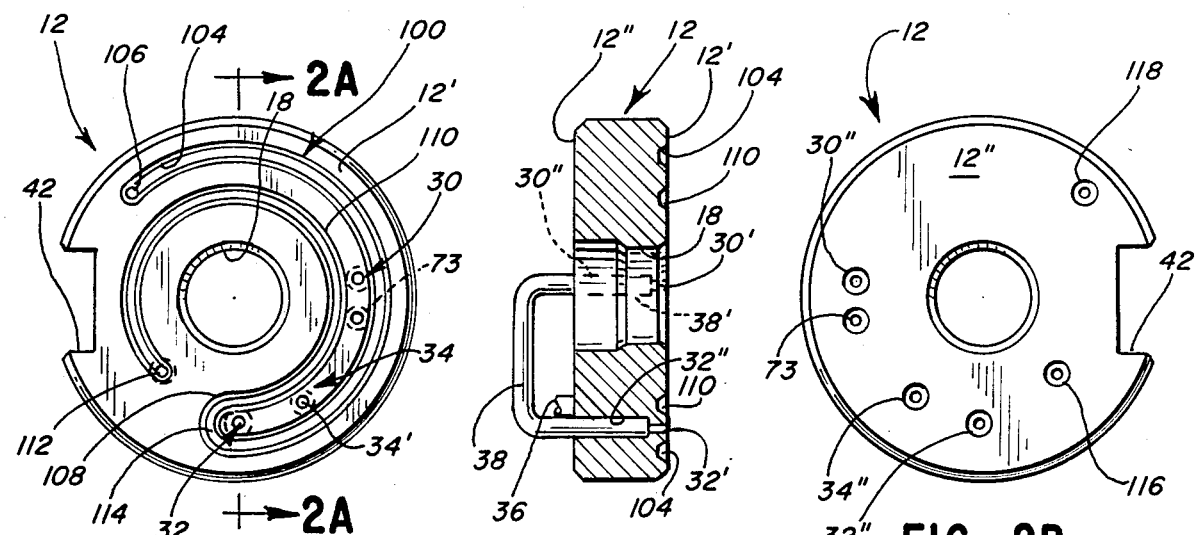
FIGS. 2, 2A and 2B, respectively, illustrates the inner face, a side elevational sectional view taken along lines 2A—2A of FIG. 2 and an outer face view of one of the respective stationary members of the valve assembly according to the invention.
Figure 3:
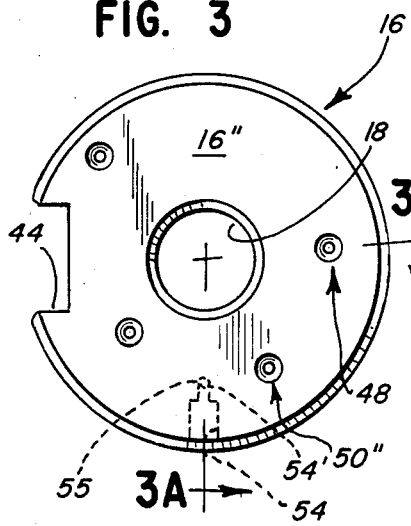
FIGS. 3, 3A and 3B, respectively, illustrate the outer face, a side elevational sectional view taken along lines 3A—3A of FIG. 3 and the inner face, respectively, of the other one of the stationary members of the valve assembly according to the invention.
Figure 3A:
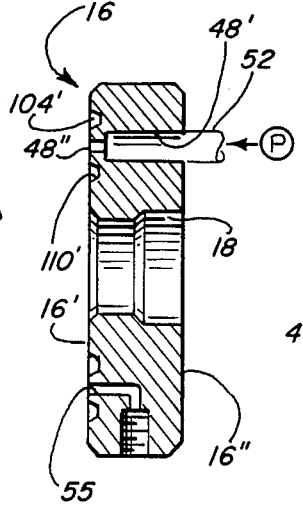
Figure 3B:
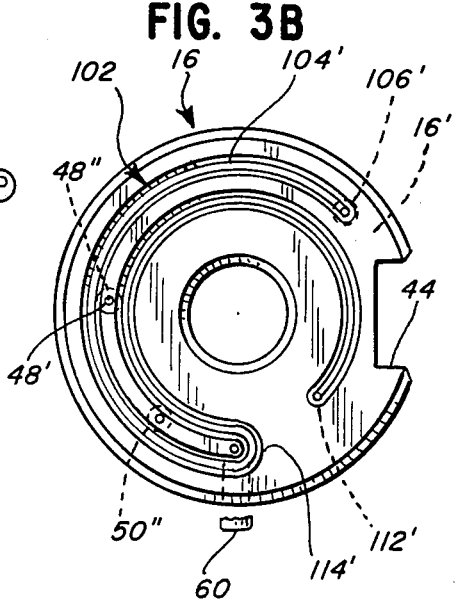
Figures 4, 4A, 4B:
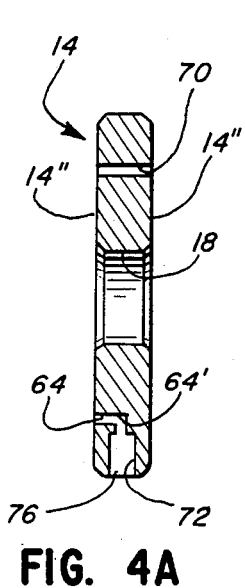
FIGS. 4, 4A and 4B respectively illustrate the one face, a side elevational view taken along lines 4A—4A of FIG. 4, and the opposite face of the center inner movable member, respectively, of the valve assembly according to the invention.

Attention now is directed to FIGS. 2 and 2A, as well as FIGS. 3A and 3B wherein there is illustrated, as formed in the faces 12' and 16' of the valve elements 12 and 16 respectively, the continuous cleaning channels 100 and 102 which are similar in configuration. Channel 100 is formed in the face 12' and consists of a first or outer groove 104 beginning at passage 106 and extending in a clockwise direction to a location 108 approximately 245° of rotation from its point of origin. The 245° extension of the channel 100 is placed precisely on face 12' so that no portion of channel 100 is exposed regardless of the angular position of member 14. The second or inner groove 110 follows a path concentric to the center of the face 12' and to the outer groove 104. The groove 110 extends counterclockwise along a path toward passage or bore 112. The grooves 104 and 110 are formed along the greater portions of a pair of concentric circles and spaced radially apart a distance of 0.04 radians along a line taken from the center of the face 12'. Bridging or connecting channel or groove 114 completes the continuous channel 100 connecting the inner and outer portions thereof. The opposite sides of both channels 100 and 102 are chamfered at about 45°. An axial bore 112 is formed in the disc 12 and opens to larger diameter coaxial passage 116. Bore 112 is located at the terminus of the inner portions of continuous channel 100. The axial bore 106 is located at the beginning of the outer portion of the continuous channel 100. The center of axial bore 112 is offset from the center of the channel portion 100. Channel 102 is identical to channel 100 and is illustrated in FIG. 3B.

The continuous cleaning channel 102 formed in face 16' of member 16 is substantially identical to the configuration of channel 100. Channel 102 is formed of outer channel 104' and inner channel 110' originating from bore 106' and terminating at bore 112' and joined by arcuate groove 114'. The channels 104', 110' and 114' are chamfered along their sides in the same manner as continuous cleaning channel 100.

In the embodiment illustrated herein, the entry of rinse fluid, generally occuring as a part of the backwash cycle, is effected via passage 118, bore 106 entering the outer portion 104 of the continuous channel 100 and exiting at the passage 116. The chamfered walls of the continuous channel 100 affords smooth flow of rinsing liquids through said channel, washing free any material which may have been collected on said walls or within the channel.

The continuous cleaning channels 100, 102 isolate the junctions of the respective segmenting passageways 66, 68, 69 and 70 from the periphery of the respective faces 12' and 16' which frictionally engage faces 14' and 14" of the central rotatable member 14. Continuous cleaning channel 100 of like configuration and path also may be provided in respective opposite faces of the center valve element 14 if desired. The rinsing step of the valve operation may be effected at the same time as the backwash operation cycle of the liquid transfer system.

It should be understood that the invention contemplates the provision of the continuous cleaning channel of the invention in other than a valve where the measuring passageways are in other than series connection; in a valve where more than one pair of volumes or measuring chambers are provided and it is not required to be limited to measurement of identical volumes of samples or identical volumes of diluent.

What we claim:

1. In a liquid diluting and transfer valve assembly of the type which includes at least a pair of valve elements, each being frictionally movable one relative to the other and having faces slidably engaged for such frictional movement, each valve element having axial measuring and segmenting passageways therethrough arranged for selective communication when at least one valve element is rotated, the junction of said passageways being at the said faces, the improvement comprising a continuous channel formed in one of said faces along a path extending substantially along the periphery of said face but spaced inwardly thereof, said channel being non-interferent with any of the passageway openings and being spaced from and not in normal operative communication with said passageways, said channel capable of intercepting any liquid traversing the faces, said channel having an inlet, an outlet and bore means formed in said valve means communicating with said inlet and outlet and capable respectively of receiving and discharging rinse liquid from a source thereof, flushing said channel of any material accumulating therein, said channel being in substantially constant communication with said inlet and said outlet.

2. The transfer valve assembly as claimed in claim 1 in which said channel is of uniform cross section along its length.

3. The transfer valve assembly as claimed in claim 1 in which said channel includes inner and outer portions formed along the greater portion of concentric circles.

4. The transfer valve assembly as claimed in claim 1 in which one of said inlet and outlet are offset relative to the center line axis taken along said channels.

5. The transfer valve assembly as claimed in claim 1 in which the inner and outer portions of said channel comprises grooves equispaced radially.

6. The transfer valve assembly as claimed in claim 1 in which the walls of the continuous channel are chamfered to facilitate flow of liquid therein during the rinsing of the cleaning channel.

7. The transfer valve assembly as claimed in claim 1 in which the inner channel portion and the outer channel portion are concentric relative the center of said face.

8. The transfer valve assembly as claimed in claim 1 in which the continuous cleaning channel is formed on the faces of oppositely disposed valve elements.

9. The transfer valve assembly as claimed in claim 1 in which there are three valve elements, the outer valve elements having faces engaged frictionally with the opposite faces of the inner member, the inner member being rotatable, with the channel formed in at least one of the engaged faces of the outer pair of said valve elements.

10. The transfer valve assembly as claimed in claim 1 in which there are two outer valve elements sandwiching an intermediate rotatable valve element, said valve elements being frictionally engagable face to face, the intermediate element carrying the segmenting passageways, said channel being formed in one of the faces of the outer elements which is frictionally engaged with a face of said intermediate valve element.

11. The transfer valve assembly as claimed in claim 10 in which said channel is formed in the faces of both outer elements which are frictionally engagable with the respective faces of said intermediate element.

* * * * *